United States Patent [19]

Kreek et al.

[11] Patent Number: 4,987,136
[45] Date of Patent: Jan. 22, 1991

[54] METHOD FOR CONTROLLING GASTROINTESTINAL DYSMOTILITY

[75] Inventors: Mary J. Kreek; Jack Fishman, both of New York, N.Y.

[73] Assignee: The Rockefeller University, New York, N.Y.

[21] Appl. No.: 828,533

[22] Filed: Feb. 12, 1986

Related U.S. Application Data

[63] Continuation of Ser. No. 680,230, Dec. 10, 1984, abandoned, which is a continuation of Ser. No. 464,110, Feb. 4, 1983, abandoned, which is a continuation-in-part of Ser. No. 358,820, Mar. 16, 1982, abandoned.

[51] Int. Cl.$^5$ .............................................. A61K 31/44
[52] U.S. Cl. ..................................... 514/282; 514/867
[58] Field of Search ............................... 514/307, 282

[56] References Cited

U.S. PATENT DOCUMENTS

| | | | |
|---|---|---|---|
| 3,254,088 | 5/1966 | Lewenstein | 424/260 |
| 3,320,262 | 5/1967 | Lewenstein | 424/260 |
| 3,332,950 | 7/1967 | Blumberg et al. | 424/260 |
| 3,896,226 | 7/1975 | Fishman | 424/260 |
| 4,176,186 | 11/1979 | Goldberg et al. | 424/260 |
| 4,272,541 | 6/1981 | Kotick et al. | 424/260 |

OTHER PUBLICATIONS

Snape, Jr. et al., –Motility of the Digestive Tract, Edited by M. Wienbeck, Raven Press, New York 1982, pp. 123–126.

Hahn et al., –Life Sciences, vol. 31, pp. 1385–1388.

J. Pharm. Exp. Ther. 169:39–45, (1969) Takemori et al.

Ward et al.–The Journal of Pharmacology and Experimental Therapeutics, vol. 224, No. 2, pp. 359–363.

Arch. Gen. Psychiatry, vol. 40, Jun. 1983, 613–617, Science, vol. 199, 10 Mar. 1978, 1093–1095.

J. M. Van Nueten, P. A. J. Janssen and J. Fontaine, Naloxone Reverses Inhibitory Effects of Fatigue and of Compounds not Related to Narcotic Analgesics in the Guinea-Pig Ileum ($^1$), Arch. int. Pharmacodyn. 220, 349–350 (1976).

Seymour Ehrenpreis, Joel Greenberg and Joseph E. Comaty, "Mechanism of Development of Tolerance to Injected Morphine by Guinea Pig Ileum", Life Sciences, vol. 17, pp. 49–54, May 24, 1975.

J. M. Van Nueten and H. Lal, "Naloxone-Induced Facilitation of Contractions, Spontaneous Activity and Tolerance to Morphine in Ileum of Morphine-Dependent Guinea-Pigs", (1974) Arch. int. Pharmacodyn, 208, pp. 378–382.

A. E. Takemori, Harvey J. Kupferberg and Jack W. Miller, "Quantitative Studies of the Antagonism of Morphine by Nalorphine and Naloxone", May 31, 1969, The Journal of Pharmacology and Experimental Therapeutics, vol. 100, No. 1, pp. 39–45.

Josef Donnerer & Fred Lembeck, "The Models for the Evaluation of Opioid Effects in the Guinea-Pig Ileum", 1985, Br. J. Pharmac., vol. 85, pp. 61–64.

Josef Donnerer, Peter Holzer & Fred Lembeck, "Release of Dynorphin, Somatostatin and Substance P from the Vascularly Perfused Small Intestine of the Guinea-Pig During Peristalsis", 1984, J. of Pharmac., vol. 83, 919–925.

William M. Yau, Patricia F. Lingle, and Michael L. Youther, "Interaction of Enkephalin and Caerulein on Guinea Pig Small Intestine", Aug. 1982, American Physiological Society, pp. 65–70.

Eva Seidl and Rudiger Schulz, "Selective Opiate Tolerance in the Guinea-Pig Ileum is not Associated with Selective Dependence", Life Sciences, vol. 33, 1983, pp. 357–360.

J. C. Szerb, "Correlation Between Acetylcholine Release and Neuronal Activity in the Guinea-Pig Ileum Myenteric Plexus; Effect of Morphine", 1982, Neuroscience, vol. 7, No. 2, pp. 327–340.

W. Kromer and H. Schmidt, "Opioids Modulate Intestinal Peristalsis at a Site of Action Additional to that Modulating Acetylcholine Release", Jul. 2, 1982, The Journal of Pharmacology and Experimental Therapeutics, vol. 223, pp. 271–274.

S. Tachibana, K. Araki, S. Ohya & S. Yoshida, "Isolation and Structure of Dynorphin, an Opioid Peptide, from Procine Duodenum", 1982, Nature, vol. 295, pp. 339–340.

Harry O. J. Collier, Nigel J. Cuthbert & David L. Francis, "Model of Opiate Dependence in the Guinea-Pig Isolated Ileum", Br. Jn. of Pharmac. (1981) vol. 73, pp. 921–932.

H. W. Kosterlitz, J. A. H. Lord, S. J. Paterson & Angela A. Waterfield, "Effects of Changes in the Structure of Enkephalins and of Narcotic Analgesic Drugs on Their Interactions with $\mu$–and $\delta$–Receptors", Br. Jn. of Pharmac. (1980), vol. 68, pp. 333–342.

H. W. Kosterlitz, R. J. Lydon and A. J. Watt, "the Effects of Adrenaline, Non-Adrenaline and Isoprenaline on Inhibitory $\alpha$–and $\beta$–adrenoceptors in the Longitudinal Muscle of the Guinea-Pig Ileum", Br. J. Pharmac (1970) vol. 39, pp. 398–413.

H. W. Kosterlitz and A. Louise Cowie, "Some Aspects of Transmission at the Nerve-Smooth Muscle Junction in the Longitudinal Muscle of the Guinea-Pig Ileum", American Journal of Digestive Diseases, New Series, vol. 13, No. 5, 1968, pp. 415–417.

H. W. Kosterlitz and A. J. Watt, "Kinetic Parameters of Narcotic Agonists and Antagonists with Particular Reference to N'Allylnoroxymorphone (Naloxone)", Br. J. Pharmac., (1968) vol. 33, pp. 266–276.

H. W. Kosterlitz and R. J. Lydon, "The Actions of choline, Adrenaline and Phenoxybenzamine on the Innervated Longitudinal Muscle Strip of the Guinea–

(List continued on next page.)

Primary Examiner—Frederick E. Waddell
Attorney, Agent, or Firm—Klauber & Jackson

[57] ABSTRACT

Method for controlling gastrointestinal dysmotility in humans by administration of opioid antagonists.

24 Claims, No Drawings

OTHER PUBLICATIONS

Pig Ileum", Br. J. Pharmac., (1968), vol. 32, pp. 422–423P.

A. Louise Cowie, H. W. Kosterlitz and A. J. Watt, "Mode of Action of Morphine-Like Drugs on Autonomic Neuro-effectors", Nature, vol. 220, Dec. 7, 1968, pp. 1040–1042.

Bert, K. B. Lum, M. H. Kermani and Richard D. Heilman, "Intestinal Relaxation Produced by Sympathomimetic Amines in the Isolated Rabbit Jejunum: Selective Inhibition by Adrenergic Blocking Agents and by Cold Storage", The Journal of Pharmac. and Experimental Therapeutics, vol. 154, No. 3, pp. 463–471, (1966).

E. A. Gyang and H. W. Kosterlitz, "Agonist and Antagonist Actions of Morphine-Like Drugs on the Guinea-Pig Isolated Ileum", Br. J. Pharmac. Chemother. (1966), vol. 27, pp. 514–527.

W. R. Martin and C. W. Gorodetzky, "Demonstration of Tolerance to and Physical Dependence on N-Allylnormorphine (Nalorphine)", The J. of Pharmac. and Experimental Therapeutics, (1965), vol. 150, No. 3, pp. 437–442.

W. D. M. Paton, "A Theory of Drug Action Based on the Rate of Drug-Receptor Combination", Proc. Rog. Sie., (1961), vol. 154, pp. 21–69.

H. W. Kosterlitz and Judith A. Robinson, "Inhibition of the Peristaltic Reflex of the Isolated Guinea-Pig Ileum", J. Physiol. (1957), vol. 136, pp. 249–262.

W. D. M. Paton, "The Action of Morphine and Related Substances on Contraction and on Acetylcholine Output of Coaxially Stimulated Guinea-Pig Ileum", Brit. J. Pharmac. (1957), vol. 11, pp. 119–127.

W. D. M. Paton, "The Response of the Guinea-Pig Ileum to Electrical Stimulation by coaxial Electrodes", Proceedings of the Physiological Society, Dec. 10–11, 1954, pp. 40–41P.

Louis Lasagna, "Drug Interaction in the Field of Analgesic Drugs", Proc. of the Royal Soc. of Medicine, vol. 58, pp. 978–983.

N. Ambache, "Separation of the Longitudinal Muscle of the Rabbit's Ileum as a Broad Sheet", Proc. of the Physiol. Society, Jul. 2–3, 1954.

Howd, et al. "Naloxone and Intestinal Motility", Experientia 34/10, pp. 1310–1311, Oct. 15, 1978.

Kromer et al., "Opioids Modulate Periodicity Rather than Efficacy of Peristaltic Waves in the Guinea Pig Ileum in Vitro", Life Sciences, vol. 26, pp. 1857–1965.

Kromer, et al., "In Vitro Evidence for the Participation of Intestinal Opioids in the Control of Peristalsis in the Guinea Pig Small Intestine", Nancy Schmiedeberg's Arch. Pharmacol. 309, 153–157 (1979).

Kadlec et al., Life Sciences, vol. 27, pp. 1557–1562 (1980).

Schulz, et al., "Centrally and Peripherally Mediated Inhibition of Intestinal Motility of Opioids", Nancy Schmiedeberg's Arch. Pharmacol, 308,255–260 (1979).

Daniela Parolaro, et al., European Journal of Pharmacology, 46 pp. 329–338, (1977).

Hellstrom, et al., "Effects of Neurotensin, Substance P and Methionine-Enkephalin on Colonic Motility", Acta Physiol Scand. pp. 147–154 (1981).

Konturek, et al., "Influence of Methionine-Enkephalin and Morphine on Myoelectric Activity of Small Bowel", AMJ Physiol. 238 (Gastrointest. Liver Physiol. 1):G384–G389 (1980).

Wong et al., European Journal of Pharmacology, 73, pp. 11–19, (1981).

Bueno, et al., European Journal of Pharmacology, 75, pp. 239–245, (1981).

Ingram, et al., "Effect of Opiates on Gastroduodenal Motility following Sugical Operation", Digestive Diseases and Sciences, New Series, vol. 26, No. 11, pp. 989–992, (Nov. 1981).

Clark et al., "Peristalsis Abolishes the Release of Methionine-Enkephalin from Guinea-Pig Ileum in Vitro", European Journal of Pharmacology, 70, pp. 421–424 (1981).

Kadlec et al., Life Sciences, vol. 27, pp. 1557–1562 (1980).

METHOD FOR CONTROLLING GASTROINTESTINAL DYSMOTILITY

RELATED APPLICATIONS

This application is a continuation of Ser. No. 680,230 filed Dec. 10, 1984, now abandoned, which is a continuation of Ser. No. 464,110 filed Feb. 4, 1983, now abandoned, which is a continuation-in-part of Ser. No. 358,820 filed Mar. 16, 1982 now abandoned.

DESCRIPTION OF PRIOR ART

Gastrointestinal dysmotility affects many humans and is associated with various clinical signs and syndromes. Hypomotility is associated with chronic constipation, obstipation, idiopathic abdominal distention, abdominal pain, abdominal cramps, irritable bowel syndrome, non-tropical sprue, megacolon associated with hypothyroidism, pseudo-obstruction of the gastrointestinal tract, colitis, hypomotility of the colon associated with diabetes mellitus, adult onset Hirschsprung's disease, neurological disorders, myopathic disorders, geriatric hypomotility disorders, jejunal-ileal bypass with secondary megacolon, hypomotility associated with cancer chemotherapy, hypomotility associated with severe burns and other major stresses, hypomotility associated with syndromes of depression, post-operative intestinal distension, and other pathological conditions. Gastrointestinal hypomotility disorders also include other disorders of esophogeal and gastric-motility and gastric emptying disorders such as diabetic gastric paresis, scleroderma and other disorders. Idiopathic constipation is a major health problem with affect many individuals. Millions of persons utilize laxatives, stool softeners, fiber preparations, mineral oil, gas absorbants, suppositories or enemas on a continuous basis. Partial hypomotility is a major feature of several defined gastrointestinal disorders.

Hypomotility is often associated with recurring bouts of hypermotility, the so-called intermittent hypomotility-hypermotility syndrome. Clinical manifestations of this affliction include alternate bouts of constipation and diarrhea, abdominal distention, pains and cramps, ileitis, regional enteritis, generalized irritable bowel syndrome, irritable colon syndrome, ulcerative and other forms of colitis.

Opioid antagonists are a well recognized class of chemical agents. They have been described in detail in the scientific and patent literature.

Pure opioid antagonists are agents which specifically reverse the effects of opioid agonists, bind to specific opioid receptors but have no opioid agonist activity.

This invention is concerned with the use of pure opioid antagonists in contrast to opioid agonists and agents that manifest mixed agonist-antagonist activities such as pentazocine, buprenorphine and others.

THE INVENTION

It has now been discovered that human disorders related to gastrointestinal dysmotility in humans can be improved, thereby alleviating the above noted illnesses, by administration of therapeutically effective amounts of pure opioid antagonists such as naloxone, naltrexone, nalmefene and related compounds.

The pharmaceutically active product will normally be administered orally or parenterally. In some cases both routes may be employed either sequentially or simultaneously. The dosage regimen which has been found to be most effective is about 2 to 70 mg per day. The preferred dosage for oral administration is about 10 to 50 mg per day, and for parenteral administration about 10 to 70 mg per day. For sustained release forms of the medicament, either oral or parenteral dosage forms are useful which deliver 10 to 50 mg per day. Of course sustained release forms can be prepared which will deliver proportional amounts over selected periods of time, for example 4, 6 or 12 hours. These quantities, irrespective of the method or route of administration selected, appear to provide optimum relief for adults in the 60 to 70 kg weight class. The attending physician may choose to vary the defined quantities depending on such factors as the condition being treated, and the age, weight, and general physical condition of the patient.

The principal and preferred compounds which are the subject matter of this invention are naloxone, naltrexone and nalmefene. These compounds are known narcotic antagonists. They are generally recognized as pure opioid antagonists and will be so regarded for purposes of this description. Naltrexone, however, has been described as having slight agonistic activity. Wikler, A., *Int. J. of the Addictions* 12(7) 869, 1977.

It should be noted, and is here emphasized, that the opioid antagonists as used in this invention are not used to neutralize the effect of opioid agonists such as narcotic drugs. They are used to treat clinical gastroenterologic disorders in which intestinal dysmotility is a major component. For such use they may be employed to treat intermittent or prolonged periods of hypomotility or intermittent hypomotility-hypermotility.

It has now been discovered that hypomotility arises from relative or absolute excess of one or more of the endogenous opioids at the intestinal level, in the brain or at both sites, or from abnormal binding of those endogenous opioids to their specific receptors in the intestine and/or brain, thereby causing inhibition of propulsive intestinal contractions. The use of pure opioid antagonists in accordance with this invention restores normal endogenous opioid balance and alleviates dysmotility problems.

Some humans, such as those suffering from chronic constipation, are affected with chronic hypomotility. Some individuals may suffer from hypermotility at one time and hypomotility another. As indicated above, the effect of the therapeutic agents of this invention when used as described herein is to restore the balance between available and bound opiate receptor sites thereby to restore normal motility as evidenced by relief of constipation, relief of abdominal distention or pain as illustrated in the examples.

Naloxone, naltrexone and nalmefene are representatives of known classes of compounds which are pure opioid antagonists. The compounds of the class are derivatives of morphine and codeine.

Nalmefene is typical of one useful class of compounds which are described together with their method of preparation in U.S. Pat. Ser. No. 3,896,226 which was issued on July 22, 1975. The compounds are morphine or codeine derivatives which may be represented by the formula:

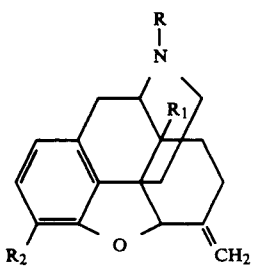

wherein R is allyl or cyclopropylmethyl, $R_1$ is hydrogen or hydroxy and $R_2$ is hydroxy or methoxy.

Typical compounds within the scope of the formula include:
a. 6-methylene-6-desoxy-N-allyl-14-hydroxydihydronormorphine.
b. 6-methylene-6-desoxy-N-cyclopropylmethyl-14-hydroxydihydronormorphine.
c. 6-methylene-6-desoxy-N-cyclopropylmethyl dihydronormorphine.
d. 6-methylene-6-desoxy-N-allyl-dihydronormorphine.
e. 6-methylene-6-desoxy-N-allyl-dihydronorcodeine.
f. 6-methylene-6-desoxy-N-cyclopropylmethyl-14-hydroxydihydronorcodeine.
g. 6-methylene-6-desoxy-N-allyl-14-hydroxydihydronorcodeine.

Compound b is nalmefene.

The compounds are prepared by reaction of the appropriate 6-keto starting compound with excess triphenylphosphomethylene followed by reaction with an allyl or cyclopropylmethyl halide, suitably the bromide or chloride. If the starting compound is a 3-hydroxy compound, i.e. a morphine derivative, the final product can be converted to a codeine derivative by reaction with diazomethane to convert the hydroxyl group to a methoxyl moiety.

Other morphine derivatives which may be employed in the practice of the invention as well as methods for their preparation are described in U.S. Pat. Nos. 3,254,088 and 3,332,950. They may be represented by the formula:

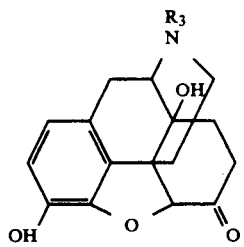

wherein $R_3$ is allyl, 3'-methyl-2'-butenyl, cyclopropylmethyl or cyclobutylmethyl.

The compounds may be prepared by reaction of a selected 14-hydroxy starting compound with a suitable organic halide such as 1-bromo-3-methyl-2-butene, allyl bromide or the corresponding chlorides.

Typical compounds within the scope of the foregoing formula include:
a. N-allyl-14-hydroxydihydronormorphinone.
b. N-cyclopropylmethyl-14-hydroxydihydronormorphinone.
c. N-cyclobutylmethyl-14-hydroxydihydronormorphinone.
d. N-(3'methyl-2-butenyl)-14-hydroxydihydronormorphinone.

The first named compound is naloxone. The second is naltrexone.

A third class of pure antagonists useful in this invention is described along with methods of preparation in U.S. Pat. Ser. No. 3,320,262. The compounds are represented by the formulas shown below in which the second formula represents dihydro compounds:

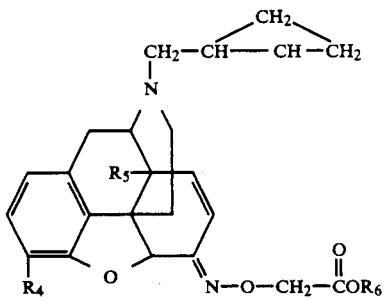

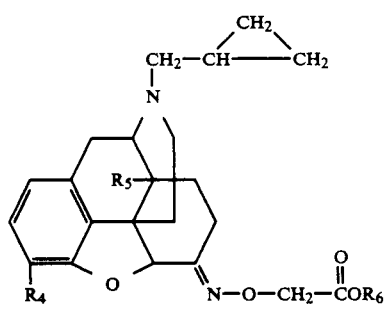

wherein $R_4$ is methoxy or hydroxy, $R_5$ is hydrogen or hydroxy and $R_6$ is hydrogen, methyl, ethyl, propyl, allyl or benzyl.

Typical compounds within the scope of the formula include:
a. N-cyclopropylmethyl-nor-14-hydroxycodeinone-6-carboxy-methyloxime.
b. N-cyclopropylmethyl-nor-codeinone-6-carboxymethyloxime.
c. N-cyclopropylmethyl-nor-14-hydroxymorphinone-6-carboxymethyloxime.
d. N-cyclopropylmethyl-nor-morphinone-6-carboxymethyloxime methylester.
e. N-cyclopropylmethyl-nor-14-hydroxydihydrocodeinone-6-carboxy-methyloxime.
f. N-cyclopropylmethyl-nor-14-hydroxydihydrocodeinone-6-carboxy-methyloxime methylester.
g. N-cyclopropylmethyl-nor-dihydrocodeinone-6-carboxymethyloxime methylester.
h. N-cyclopropylmethyl-nor-14-hydroxydihydromorphinone-6-carboxy-methyloxime methylester.
i. N-cyclopropylmethyl-nor-dihydromorphinone-6-carboxymethyloxime methylester.

The compounds are prepared by reaction of the selected ketone starting compound with a suitable organic halide as described above, followed by reaction of the N-substituted compounds with a selected ester of carboxymethoxyl amine.

All of the compounds described above can be utilized in the form of pharmaceutically acceptable salts. Pharmaceutically acceptable salts are salts which are free of toxicity or other therapeutically harmful or undesirable effects. These include, for example, such salts as the hydrochloride, hydrobromide, neutral and acid fumarate and maleate, teraphthalate, ethane sulfonate, oxalate and bitartrate.

Water-soluble salts with volatile acids (e.g. hydrochloric and acetic acid) can be prepared by adding an aqueous solution of slightly more than one equivalent of the acid to an aqueous dispersion of the base and evaporating the solution thus formed under reduced pressure. The residue can then be recrystallized. Salts of non-volatile inorganic acids (e.g. orthophosphoric acid) can be prepared by adding the stoichiometric amount of the acid to an aqueous dispersion of the base and treating the resulting solution in the same way. Salts of organic acids which are difficultly soluble in water (e.g. the benzoate) can be prepared by reacting the acid and the base in equivalent amounts in ethyl alcohol medium and evaporating the solution.

For ease of administration it is, of course, preferred to treat patients orally. Surprisingly, as is illustrated hereinafter, naloxone, which has been art recognized as being poorly absorbed when given perorally is nevertheless active at local intestinal sites and effective for the indications mentioned above when administered orally. In the event that the patient is unable to cooperate, is kept in a "nothing by mouth" status, if there is an intransigent blockage of the gastrointestinal tract, or if antagonist activity at the brain or at other systemic sites is desired, the route of choice will be the parenteral route.

The principal aspects of the invention, then, are the use of certain known compounds to achieve control of intestinal motility. The compounds may be used alone or in association with selected pharmaceutical carriers in the form of pharmaceutical compositions containing effective amounts of the active agents. The compositions may be administered parenterally or by various non-parenteral routes, primarily oral, but also by buccal, sublingual, rectal and transdermal routes. The compositions may be prepared for relatively rapid absorption or in sustained release forms.

For buccal and sublingual administration the active ingredient can be formulated in tablet form with water soluble binding agents such as lactose or other palatable carbohydrates.

For rectal administration suppositories or inserts containing the active ingredient dispersed in such reagents as cocoa butter, petroleum, or other natural lubricant or in a synthetic emmolient such as polyethylene glycol 1000 or polyethylene glycol 4000.

Transdermal administration will normally be from a sustained release preparation which may be applied as a patch or from a gauze applied to the skin.

The preferred method of administering the active agents of this invention is from sustained release forms since this is most convenient for patients, and avoids the necessity of constant clock watching or interruption of normal daily activities. A number of compositions suitable for such preparations are known and can be used in the practice of this invention. As aforesaid, the dosage forms can be prepared to deliver 10 to 50 mg of active ingredient per day divided over selected time intervals, for example 4, 6, 12 or even twenty-four hours.

One convenient procedure is to formulate the selected motility control agent in a time disintegrating tablet or pellet coated with various thicknesses of known materials such as carnauba wax, cellulose esters and ethers, fats, keratin, gluten or various natural or synthetic esters. Tablets in which the motility control agent is contained in a slowly dissolving core such as a core of stearic acid or castor oil are useful. Mixed release granule tablets comprising mixtures of the drug itself and the drug in separate particles coated with materials which dissolve at different rates such as dehydrogenated castor oil or fatty acids can also be employed. Alternatively the active material can be bound to an ion exchange resin such as sulfuric acid type cation exchange resin.

The presently preferred sustained release forms of this invention are those in which the active agent is carried through the gastrointestinal tract in a mixed polymer carrier. The carrier slowly erodes during transport so that increments of the opioid antagonist may be released for attachment to receptor sites.

In these forms, the principal carrier is a mixed, hydrated alkyl hydroxy cellulose in which the alkyl groups contain up to four carbon atoms and at least one is propyl or butyl. This polymer functions as a drug release retardant. Cellulose derivatives which are substituted with two different alkyl groups are preferred since there is less tendency for such polymers to crystallize. The polymers are prepared by standard alkoxylation reactions. In case two different alkyl groups are to be substituted, concurrent or successive reactions may be employed. Generally, with such mixed substituents there will be about 50% of each substituent. The presently preferred polymer is propyl hydroxymethyl cellulose.

The cellulose derivative is normally hydrated to a degree of from about 5% to 25% by weight, preferably 10% to 20%. A degree of hydration of 15% by weight is especially preferred since it is readily achieved, and provides sustained release forms with excellent properties.

To prevent the cellulose polymer from crystallizing and thereby reducing the rate at which the active agent is released an anticrystallinity agent is added. The function of the agent is to prevent the cellulose polymer from achieving a degree of regularity at which it will crystallize. The presently preferred anticrystallinity reagents are polyalkylene oxides, such as polyethylene oxide or other pharmaceutically acceptable analogues. The molecular weight of the oxide may vary from about 100,000 to 10 million with 4 to 5 million being preferred because of ready availability, ease of compounding and efficiency for preventing crystallization. Normally the amount of such agent added will be from about 15% to 30% by weight so that the weight of cellulose product will be from about 70% to 85%.

The polymer and selected active agent or agents are compounded, to form tablets or other standard dosage forms in conventional equipment with any of a number of anti-stick or releasing agents such as magnesium stearate or talc. The amount employed is not critical and normally ranges from about 0.5% to 2% by weight.

The sustained release dosage forms can be formulated to contain any desired quantity of active agent. Typically, a tablet or other form will contain from about 5% to 20% active ingredient and 80% to 95% carrier. As indicated above, they may be prepared to release the selected quantities of opioid antagonist over time periods of, for example, from 4 to 12 hours.

In the foregoing discussions, all quantities given on a by weight basis are based on the total weight except the degree of hydration of the cellulose derivative which is based on the weight of the derivative.

In short, the motility control agents of this invention can be administered in any of a wide variety of forms including tablets, capsules, lozenges, suppositories, emulsions, isotonic solutions and the like. They can be formulated for immediate absorption or for sustained release.

The following non-limiting examples are given by way of illustration only.

EXAMPLE 1

A female with a history of chronic constipation for a period of over twenty years, requiring daily use of large doses of laxatives plus frequent enemas, was admitted to the research hospital on day one at approximately 4:00 p.m. She was given a standard laxative regimen documented to be inadequate to effect a spontaneous bowel movement, and placed on a high residue diet.

During the first 24 hours she was treated with a placebo (Infusion A) according to the following schedule:

| 4 p.m.–5 p.m. | (1) Dextrose and water | 250 cc over 1 hr. |
|---|---|---|
| 5 p.m.–12 midnight | (2) Saline | 250 cc over 7 hrs. |
| 12 midnight–8 a.m. | (3) Dextrose and water | 250 cc over 8 hrs. |
| 8 a.m.–4 p.m. | (4) Dextrose and water | 250 cc over 8 hrs. |
| | | 1250 cc over 24 hrs. |

On day two at 4:00 p.m. the placebo was terminated and the patient was treated intravenously with naloxone according to the following schedule.

| 4 p.m.–5 p.m. | (1) Dextrose & Water | 250 cc + 1.6 mg Naloxone in 1 hr. |
|---|---|---|
| 5 p.m.–12 midnight | (2) Saline | 250 cc + 8.4 mg Naloxone in 7 hrs. |
| 12 midnight–8 a.m. | (3) Dextrose & Water | 250 cc + 9.6 mg Naloxone in 8 hrs. |
| 8 a.m.–4 p.m. | (4) Dextrose & Water | 500 cc + 9.6 mg Naloxone in 8 hrs. |
| | | 1250 cc + 29.2 mg Naloxone in 24 hrs. |

At 4:00 p.m. on day three the parenteral administration was discontinued and the dosage regimen was changed to oral administration of 3.6 mg of naloxone in synthetic grape juice every three hours for three days, omitting treatment only when the patient was sleeping. The total dosage per day was 21.6 mg.

During the five days that the patient was under hospital care the stools were collected and weighed. The results were as follows:

| | STOOL WEIGHT GRAMS | |
|---|---|---|
| Day | Wet Weight | Dry Weight |
| 1 | 452 | 41 |
| 2 | 649 | 52 |
| 3 | 985 | 77 |
| 4 | 997 | 77 |
| 5 | 806 | 65 |

Samples of the patient's blood and urine were collected each day and subjected to analysis. No adverse effects were observed.

The experiment was conducted as a single blind. The patient was not aware of whether she was receiving a placebo or the active agent.

EXAMPLE II

A second patient with a history of over twenty years of chronic constipation, intractable to laxatives, who for the past several months was only relieved by enema treatment was admitted to the hospital and placed on a high residue diet.

She was then treated in a manner similar to the patient of Example I, but with no laxatives or enemas given, in accordance with the following schedule:

| DAY | TREATMENT |
|---|---|
| 1 | 29.2 mg naloxone, intravenous |
| 2 | placebo, oral |
| 3 | 14.4 mg naloxone, oral |
| 4 | 21.6 mg naloxone, oral |
| 5 | 21.6 mg naloxone, oral |
| 6 | 7.2 mg naloxone, oral |
| 7 | placebo, oral |
| 8 | placebo, oral |
| 9 | placebo, oral |

The patient's stools were collected and weighed each day with the following results:

| | STOOL WEIGHT GRAMS | |
|---|---|---|
| DAY | WET WEIGHT | DRY WEIGHT |
| 1 | 84 | 18.5 |
| 2 | none | — |
| 3 | 35 | 8.2 |
| 4 | 125 | 66.4 |
| 5 | 230 | 82.4 |
| 6 | 34 | 12.1 |
| 7 | none | — |
| 8 | 43 | 12.2 |
| 9 | none | — |

No adverse effects were noted by clinical examinations, blood or urine analysis.

The following tables summarize the results which were achieved with additional patients treated with nalaxone following the general procedures of Examples I and II. Substantially the same results will be achieved with naltrexone, nalmefene and other compounds within the scope of the foregoing formulas.

The tables set forth the significant details and results of a number of studies conducted with different patients suffering from various forms of intestinal dysmotility. For example, Table 1 reports the results of five separate studies, three inpatient and two outpatient, on the same patient at the research hospital. The first study was of two days duration. The lengths of subsequent studies are as indicated.

The reports Tables 1 to 5 are for patients with chronic constipation. Those in Tables 6, 7 and 8 are for patients with irritable bowel syndrome. Tables 9 and 10 are summaries.

TABLE 1

Patient Number 1
A.O., a 53 year old female

| Study | Route of Administration | Study Day | Active Compound or Placebo | Total 24 Hr. Dose (mg) | Fecal Wet Wt. (gm) | Fecal Dry Wt. (gm) | Fecal Fat (%) | Symptoms, Signs, Comments |
|---|---|---|---|---|---|---|---|---|
| #1 (inpatient) | i.v. | 1 | P | — | 452 | 41 | 1.8 | no change |
|  |  | 2 | A | 29.2 | 649 | 52 | 3.0 | marked improvement |
| #2 (inpatient) | p.o. | 1 | A | 21.6 | 985 | 77 | 4.7 | marked improvement |
|  |  | 2 | A | 21.6 | 997 | 77 | 3.3 | marked improvement |
|  |  | 3 | A | 21.6 | 806 | 65 | 2.4 | marked improvement |
| #3 (outpatient) | p.o. | 1 | A | 21.6 |  |  |  | Average day |
|  |  | 2 | A | 21.6 |  |  |  | Better than average day |
|  |  | 3 | A | 21.6 |  |  |  | Much better than average day |
|  |  | 4 | P | — |  |  |  | Average day |
|  |  | 5 | P | — |  |  |  | Bad day |
|  |  | 6 | P | — |  |  |  | Bad day |
| #4 (inpatient) | i.v. | 1 | neither | — | 336 | 15 | 2.6 |  |
|  |  | 2 | A | 29.2 | 775 | 199 | 5.7 |  |
|  |  | 3 | A | 29.2 | 859 | 212 | 4.1 |  |
| #5 (outpatient) |  | 1 | A | 21.6 |  |  |  | Much better than average |
|  |  | 2 | A | 21.6 |  |  |  | Much better than average |
|  |  | 3 | A | 21.6 |  |  |  | Much better than average |
|  |  | 4 | P | — |  |  |  | Average (diarrhea) |
|  |  | 5 | P | — |  |  |  | Worse than average |

TABLE 2

Patient Number 2
B.K., a 39 year old female

| Study | Route of Administration | Study Day | Active Compound or Placebo | Total 24 Hr. Dose (mg) | Fecal Wet Wt. (gm) | Fecal Dry Wt. (gm) | Fecal Fat (%) | Symptoms, Signs, Comments |
|---|---|---|---|---|---|---|---|---|
| #1 | — | 1 | neither | 0 |  |  |  |  |
|  |  | 2 | A | 29.2 | 84 | 18.5 | 3.6 |  |
|  |  | 3 | P | 0 | — | — | — | no stool |
| #2 | — | 1 | A | 14.4 | 35 | 8 | 1.1 |  |
|  |  | 2 | A | 21.6 | 125 | 66 | 5.9 |  |
|  |  | 3 | A | 21.6 | 230 | 82 | 9.0 |  |
|  |  | 4 | A | 7.2 | 34 | 12 | 0.8 |  |
|  |  | 5 | P | 0 | — | — | — | no stool |
|  |  | 6 | P | 0 | 43 | 7 | 0.9 |  |
|  |  | 7 | P | 0 | — | — | — | no stool |
|  |  | 8 | P | 0 | 30 | 7 | 0.8 |  |
|  |  | 9 | — | 0 | 37 | 10 | 0.9 |  |

TABLE 3

Patient Number 3
J.P., a 39 year old male

| Study | Route of Administration | Study Day | Active Compound or Placebo | Total 24 Hr. Dose (mg) | Fecal Wet Wt. (gm) | Fecal Dry Wt. (gm) | Fecal Fat (%) | Symptoms, Signs, Comments |
|---|---|---|---|---|---|---|---|---|
| #1 | i.v. | 1 | A | 29.2 | — | — | — | no stool |
|  |  | 2 | P | — | — | — | — | no stool |
|  |  | 3 | — | — | — | — | — | no stool |
|  |  | 4 | — | — | — | — | — | no stool |
|  |  | 5 | — | — | — | — | — | no stool |
| #2 | p.o. | 1 | — | — | — | — | — | no stool |
|  |  | 2 | — | — | — | — | — | no stool |
|  |  | 3 | — | — | — | — | — | no stool |
|  |  | 4 | — | — | — | — | — | no stool |
|  |  | 5 | A | 21.6 | — | — | — | no stool |
|  |  | 6 | A | 21.6 | — | — | — | no stool |
|  |  | 7 | A | 21.6 | — | — | — | no stool |
|  |  | 8 | P | — | — | — | — | no stool |
|  |  | 9 | P | — | — | — | — | no stool |
|  |  | 10 | P | — | — | — | — | no stool |

TABLE 4

Patient Number 7
B.B., a 65 year old female

| Study | Route of Administration | Study Day | Active Compound or Placebo | Total 24 Hr. Dose (mg) | Fecal Wet Wt. (gm) | Fecal Dry Wt. (gm) | Symptoms, Signs Comments |
|---|---|---|---|---|---|---|---|
| #1 (in-patient) | i.v. | 1 | A | 29.2 | 166 | 59 | cramps; improvement spontaneous passage of stool |
|  |  | 2 | P | — | 205 | 42 | average; digital removal of stool |
| #2 (in-patient) | p.o. | 1 | A | 21.6 | — | missing | no stool |
|  |  | 2 | A | 21.6 | 238 | 35 | improvement; "natural easy BM's" |
|  |  | 3 | A | 21.6 | 262 | 35 | marked improvement; spontaneous "natural BM's" |
|  |  | 4 | A | 21.6 | 145 | 20 | marked improvement; spontaneous "natural BM's" |
|  |  | 5 | P | — | 265 | 23 | marked improvement; spontaneous "natural BM's" |
|  |  | 6 | P | — | 299 | 36 | marked improvement; spontaneous "natural BM's" |
|  |  | 7 | P | — | 166 | 38 | less improvement; less BM; still spontaneous |
|  |  | 8 | P | — | 105 | 11 | BM only with digital removal; back to average |
|  |  | 9 | — | — | — | — | No BM even after attempt at digital removal |
| #3 (in-patient) | i.v. | 1 | P | — | — | — |  |
|  |  | 2 | P | — | 135 | 17 | removal by digital manipulation |
|  |  | 3 | A | 29.2 | — | — |  |
|  |  | 4 | A | 29.2 | 183 | 24 | Spontaneous BM; some of feces lost because of sudden urge to pass BM |

TABLE 5

Patient Number 8
H.D., a 71 year old male

| Study | Route of Administration | Study Day | Active Compound or Placebo | Total 24 Hr. Dose (mg) | Fecal Wet Wt. (gm) | Fecal Dry Wt. (gm) | Symptoms, Signs Comments |
|---|---|---|---|---|---|---|---|
| #1 | i.v. | 1 | P | — | 144 | 12 |  |
|  |  | 2 | A | 29.2 | 281 | 17 | marked improvement |
| #2 | p.o. | 1 | A | 21.6 | 135 | 7 | marked improvement |
|  |  | 2 | A | 21.6 | 134 | 14 | marked improvement |
|  |  | 3 | A | 21.6 | 476 | 29 | marked improvement |
|  |  | 4 | P | — | — | — | spontaneous BM; but feces lost by patient because of sudden urge to pass BM |
|  |  | 5 | P | — | 554 | 26 | improvement |
|  |  | 6 | P | — | 114 | 9 | strain to pass stool |

TABLE 6

Patient Number 4
B.S., a 68 year old male

| Study | Route of Administration | Study Day | Active Compound or Placebo | Total 24 Hr. dose (mg) | Fecal Wet Wt. (gm) | Fecal Dry Wt. (gm) | Fecal Fat (%) | Symptoms, Signs, Comments |
|---|---|---|---|---|---|---|---|---|
| #1 (in-patient) | i.v. | 1 | — | — | 21 | 2.0 | 0.7 | pain; usual type of bad day |
|  |  | 2 | A | 29.2 | 14 | 1.0 | 0.3 | marked improvement; pain; much better than average |
|  |  | 3 | P | — | 43 | 4.0 | 6.4 | sustained improvement; pain; much better than average |
| #2 (out-patient) | p.o. | 1 | A | 21.6 |  |  |  | marked improvement; no pain; full BM |
|  |  | 2 | A | 21.6 |  |  |  | no records kept; grandchild's death |
|  |  |  | grandchild died; postponed trial for 2 days |  |  |  |  |  |
|  |  | 3 | A | 21.6 |  |  |  | marked improvement; full BM; no pain |
|  |  | 4 | P | — |  |  |  | marked improvement; no pain; considerable gas; full BM |
|  |  | 5 | P | — |  |  |  | some improvement; no pain; considerable gas |
|  |  | 6 | P | — |  |  |  | average day; abdominal distension; gas; difficulty passing BM |

TABLE 6-continued

Patient Number 4
B.S., a 68 year old male

| Study | Route of Administration | Study Day | Active Compound or Placebo | Total 24 Hr. dose (mg) | Fecal Wet Wt. (gm) | Fecal Dry Wt. (gm) | Fecal Fat (%) | Symptoms, Signs, Comments |
|---|---|---|---|---|---|---|---|---|
| #3 (Out-patient) | p.o. | 1 | P | — | | | | pain; distention; poor day |
| | | 2 | P | — | | | | problem with passing BM; pain; average day |
| | | 3 | P | — | | | | pain; problem passing BM; average day |
| | | 4 | P | — | | | | pain; problem passing BM; average day |
| | | 5 | P | — | | | | pain; problem passing BM; average day |
| | | 6 | A | 14.4 | | | | pain; problem passing BM; average day |
| | | 7 | A | 21.6 | | | | good BM; no pain; marked improvement |
| | | 8 | A | 21.6 | | | | good BM; followed later by pain; some improvement |
| | | 9 | A | 21.6 | | | | good BM; no pain; marked improvement |
| | | 10 | A | 10.8 | | | | good BM; no pain; marked improvement |
| | | 11 | A | 18.0 | | | | good BM; some pain; some gas |
| #4 (out-patient) | p.o. | 1 | A | 7.2 | | | | pain; distention; average day |
| | | 2 | A | 18.0 | | | | pain; distention; average day |
| | | 3 | A | 21.6 | | | | pain; spontaneous BM; slight improvement |
| | | 4 | A | 18.0 | | | | pain; distention; some improvement |
| | | 5 | A | 21.6 | | | | no pain; minimal distention; marked improvement |
| | | 6 | P | — | | | | no pain; some distention; some improvement |
| | | 7 | P | — | | | | distention; recurrent pain |
| | | 8 | P | — | | | | abdominal pain; some distention; slight improvement |
| | | 9 | P | — | | | | distention; no pain; slight improvement |

TABLE 7

Patient Number 5
J.B., a 19 year old female

| Study | Route of Administration | Study Day | Active Compound or Placebo | Total 24 Hr. dose (mg) | Fecal Wet Wt. (gm) | Fecal Dry Wt. (gm) | Fecal Fat (%) | Symptoms, Signs, Comments |
|---|---|---|---|---|---|---|---|---|
| #1 (in-patient) | i.v. | 1 | A | 29.2 | 61 | 14 | 2.6 | less distention; better than average day |
| | | 2 | P | — | 648 | 204 | 5.7 | less distention; better than average day |
| #2 (out-patient) | p.o. | 1 | A | 10.8 | 253 | 75 | 0.8 | less distention |
| | | 2 | A | 21.6 | | | | marked improvement; spontaneous BM |
| | | 3 | A | 21.6 | | | | spontaneous BM; some distention |
| | | 4 | P | — | | | | distention; pain; cramps; marked deterioration |
| | | 5 | P | — | | | | spontaneous BM; some pain; distention |
| | | 6 | P | — | | | | distention; spontaneous BM |
| #3 (in-patient) | i.v. | 1 | P | — | 12 | 1 | | no change |
| | | 2 | A | 29.2 | 96 | 31 | | much less distention; spontaneous passage of multiple soft BM |
| #4 (out-patient) | p.o. | 1 | A | 21.6 | | | | 3 BM passed; no pain; no distention |
| | | 2 | A | 21.6 | | | | 3 BM soft passed; no pain; no distention |
| | | 3 | A | 21.6 | | | | 2 BM soft passed; some cramps; no distention |
| | | 4 | P | — | | | | small hard BM passed; distention |
| | | 5 | P | — | | | | 2 small BM; pain; distention |

TABLE 7-continued

Patient Number 5
J.B., a 19 year old female

| Study | Route of Administration | Study Day | Active Compound or Placebo | Total 24 Hr. dose (mg) | Fecal Wet Wt. (gm) | Fecal Dry Wt. (gm) | Fecal Fat (%) | Symptoms, Signs, Comments |
|---|---|---|---|---|---|---|---|---|
| | | 6 | P | — | | | | 2 small BM; pain; distention |

TABLE 8

Patient Number 6
A.S., a 66 year old male

| Study | Route of Administration | Study Day | Active Compound or Placebo | Total 24 hr. Dose (mg) | Fecal Wet Wt. (gm) | Fecal Dry Wt. (gm) | Fecal Fat (%) | Symptoms, Signs, Comments |
|---|---|---|---|---|---|---|---|---|
| #1 (inpatient) | i.v. | 1 | A | 29.2 | — | — | — | no BM; marked improvement with decreased pain and distention |
| | | 2 | P | — | 21 | 4 | 1.6 | BM small; decreased pain and distention |
| #2 (outpatient) | | 1 | A | 18.0 | 60 | 14 | 2.1 | spontaneous BM; no distention; marked improvement |
| | | 2 | A | 21.6 | 44 | 6 | 2.3 | spontaneous BM; no distention; marked improvement |
| | | 3 | A | 21.6 | | | | no BM; no pain or distention |
| | | 4 | A | 21.6 | | | | spontaneous BM; no symptoms |
| | | 5 | A | 21.6 | | | | no stool; no symptoms |
| | | 6 | A/P | 3.6 | | | | spontaneous BM; no symptoms |
| | | 7 | P | — | | | | no stool; average day |
| | | 8 | P | — | | | | one BM; better than average day |
| | | 9 | P | — | | | | no stool; average day |

B. Tables 9 and 10 in more compact form the date from Tables 1 to 8.

TABLE 9

Chronic Constipation Patients

| Patient Initials | Patient Number | Age | Sex | Diagnosis | Onset of Symptoms | No. of Inpatient Studies | No. of Outpatient Studies (all P.O.) | Outcome |
|---|---|---|---|---|---|---|---|---|
| A.O. | 1 | 53 | F | Non-tropical sprue | more than 40 years | 3 (2 iv; 1 po) | 2 | 5 successful trials |
| B.K. | 2 | 39 | F | Idiopathic constipation | more than 20 years | 2 (1 iv; 1 po) | 0 | 2 successful trials |
| J.P. | 3 | 39 | M | Idiopathic constipation | about 10 years | 2 (1 iv; 1 po) | 0 | No successful trials |
| B.B. | 7 | 65 | F | Idiopathic constipation | more than 50 years | 3 (2 iv; 1 po) | 1 | 2 successful trials, 1 probably successful trial |
| HD | 8 | 77 | M | Geriatric type Idiopathic constipation | about 8 years | 2 (1 iv, 1 po) | 0 | 1 successful trial; 1 probably successful trial |

TABLE 10

Irritable Bowel Syndrome Patients

| Patient Initials | Patient Number | Age | Sex | Onset of Symptoms | No. of Inpatient Studies | No. Of Outpatient Studies | Outcome |
|---|---|---|---|---|---|---|---|
| B.S. | 4 | 68 | M | more than 40 years | 1 i.v. | 3 | Successful |
| J.B. | 5 | 19 | F | more than 10 years | 2 i.v. | 2 | Successful |
| A.S. | 6 | 66 | M | about 5 years | 1 i.v. | 1 | Successful |

C. The following formulates illustrate procedures which can be employed to produce a variety of dosage forms of the active ingredients of this invention. The active ingredient in each formulation is naloxone. It could be naltrexone, nalmefene or any of the other compounds of this invention.

| TABLET | | |
|---|---|---|
| | | Mg tablet |
| (1) Oral form: | Naloxone hydrochloride | 12 |
| | Starch | 50 |
| | Lactose | 75 |
| | Magnesium stearate | 2 |
| | Stearic acid | 5 |

The compound, a portion of the starch and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearic acid, and the balance of the starch are added and the entire mix blended prior to compression on a suitable tablet press. The tablets are compressed at a weight of 232 mg using a 11/12" punch with a balance of 4 kg. These tablets will disintegrate within a half hour according to the method described in USP XVI.

| | | Mg tablet |
|---|---|---|
| (2) | Naloxone | 6 |
| | Microcrystalline cellulose | 30 |
| | Spray-dried lactose | 60 |
| | Colloidal silica | 1 |
| | Stearic acid | 1 |

Screen the alkaloid to break up lumps and blend with microcrystalline cellulose. Add spray-dried lactose and blend. Finally add the stearic acid and colloidal silica; blend to obtain homogenous mixture. Compress using 9/32 in shallow concave punch.

| CAPSULES | | |
|---|---|---|
| (1) | Naloxone hydrochloride | 10 mg. |
| | Lactose | 45 |
| | Starch | 45 |

The compound, a portion of the starch and the lactose are combined and wet granulated with starch paste. The wet granulation is placed on trays and allowed to dry overnight at a temperature of 45° C. The dried granulation is added to a hand gelatin capsule of the appropriate size.

| (2) | Naloxone | 20 mg |
|---|---|---|
| | Sesame oil | 90 |

The free base is mixed with sesame oil and encapsulated in a soft gelatin capsule of the appropriate size.

SUSTAINED RELEASE (1) Oral

Naloxone (12 mg) is included in a hydrophilic polymer matrix from which it will be gradually excluded following ingestion. The inclusion is accomplished by dissolving the free base in a suitable non-polar solvent from which it will be absorbed by the polymers. Removal of the solvent leaves the product bound in the matrix from which it is released by water solution. Rates of delivery can be controlled by the hydrophilic character of the matrix which can be both non- or biodegradable as desired.

(2) Oral

Naloxone (12 mg) is mixed with sucrose and compounded into 1 mm diameter pellets to yield a total of 200 pellets. Fifty beads are used in the uncoated form. The remaining beads are divided into three equal parts and coated with stearic acid, palmitic acid and glycerol myristate in appropriate amounts to allow dissolution in the intestine over 4, 8 or 12 hours. The beads are encapsulated in an appropriate size hard gelatin capsule.

| PARENTERAL | | |
|---|---|---|
| | | Mg/cc |
| (1) | naloxone hydrochloride | 10 |
| | Methyl paraben | 1.8 |
| | Propyl paraben | 0.2 |
| | Water for injection | q.s. |

The solution is prepared by first dissolving the parabens in hot water for injection, cooling to room temperature and dissolving the compound and sodium chloride. It is then filtered, using sterile technique, through a bacteriological filter (0.6 micron or smaller porosity), after which it is transferred into ampoules or multiple-dose vials.

| | | Mg/cc |
|---|---|---|
| (2) | Naloxone | 10 or 20 |
| | Ethanol | 100 |
| | Propylene-glycol | 880 |

The solution is prepared by dissolving the naloxone in the alcohol and diluting with propylene glycol. It is then filtered using sterile techniques, through a bacteriological filter after which it is transferred into ampules or multiple dose vials.

SUSTAINED RELEASE (1) Parenteral

The hydrochloride salt of naloxone (20 mg) is dissolved in an appropriate amount of ethanol. The solution is mixed with sesame oil (5:1 ratio) and heated at 45° under vacuum to remove the alcohol. The residue (drug in sesame oil) is transferred into individual or repeated dose ampoules.

(2) Suppository

| | Percent |
|---|---|
| Naloxone hydrochloride | 4.06 |
| Polyoxyethylene 1000 (approx M 1000) | 80.14 |
| Polyoxyethylene 4000 (approx M 4000) | 15.00 |
| Methyl paraben | .45 |
| Propyl paraben | .05 |
| Purified water USP | 3.10 |

The HCl salt of the compound is dissolved in the water and added to a melted mixture of the polyoxyethylenes which are already combined with the parabens. This molten mixture is poured into suppository molds and cast into suppositories weighing 3 grams each. They are frozen to solidify and packaged into foil.

(3) Tablet

A total of 65 gm 15% hydrated propyl hydroxymethyl cellulose and 24 gm polyethylene oxide (mw=5,000,000) are mixed together with 10 gm of naloxone hydrochloride in a uniform powdery slurry and 1 mg magnesium stearate is added. The mix is pressed into tablets at a pressure of 100 atm. Each of the tablets contains 10 mg naloxone. A tablet when orally administered delivers the naloxone over a period of 12 hours.

(4) Tablet

Nalmefene tablets which are suitable for a sustained release delivery over 12 hour periods are prepared by mixing in the conventional manner 63 gm 15% hydrated propyl hydroxymethyl cellulose and 24 gm polyethylene oxide (mw=5,000,000) together with 12 gm of nalmefene hydrochloride in a uniform powdery slurry. The mix is pressed into tablets at a pressure of 100 atm, each of the tablets containing 12 mg nalmefene.

What is claimed is:

1. A method for the relief of gastrointestinal dysmotility in a patient afflicted with an idiopathic gastrointestinal dysmotility which comprises administration of an amount which is effective to relieve said dysmotility of a compound represented by the formula:

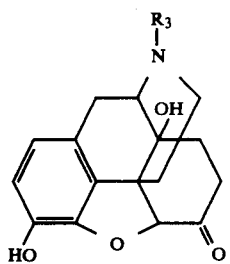

wherein R₃ is 3'-methyl-2-buteneyl; allyl; cyclopropylmethyl; or cyclobutylmethyl and pharmaceutically acceptable salts thereof.

2. A method as in claim 1 wherein the method of administration is oral and the amount administered is from about 10 to about 50 mg per day.

3. A method as in claim 1 wherein the method of administration is parenteral and the amount administered is from about 10 to about 70 mg per day.

4. A method as in claims 1, 2 or 3 wherein the compound administered is naloxone.

5. A method as in claims 1, 2 or 3 wherein the compound administered is naltrexone.

6. A method as in claims 1, 2 or 3 wherein the result of the dismotility is constipation.

7. A method as in claims 1, 2 or 3 wherein the result of the dysmotility is irritable bowel syndrome.

8. A method as in claims 1, 2 or 3 wherein the result of the dysmotility is constipation, and the compound administered in naloxone.

9. A method as in claims 1, 2 or 3 wherein the result of the dysmotility is constipation, and the compound administered is naltrexone.

10. A method as in claims 1, 2 or 3 wherein the result of the dysmotility is irritable bowel syndrome and the compound administered is naloxone.

11. A method as in claims 1, 2 or 3 wherein the result of the dysmotility is irritable bowel syndrome and the compound administered is naltrexone.

12. A method for the relief of gastrointestinal dysmotility in a patient afflicted with an idiopathic gastrointestinal dysmotility which comprises administration of an amount which is effective to relieve said dysmotility of a compound represented by the formula:

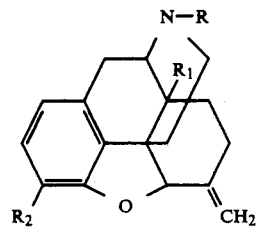

wherein R is allyl or cyclopropylmethyl, R₁ is hydrogen or hydroxy and R₂ is hydroxy or methoxy and pharmaceutically acceptable salts thereof.

13. A method as in claim 12 wherein the method of administration is oral and the amount administered is from about 10 to 50 mg. per day.

14. A method as in claim 12 wherein the method of administration is oral and the amount administered is from about 10 to 70 mg per day.

15. A method as in claims 12, 13 or 14 wherein the compound administered is nalmefene.

16. A method as in claims 12, 13 or 14 wherein the result of the dysmotility is constipation.

17. A method as in claims 12, 13 or 14 wherein the result of the dysmotility is irritable bowel syndrome.

18. A method as in claims 12, 13 or 14 wherein the result of the dysmotility is constipation, and the compound administered is nalmelfene.

19. A method as in claims 12, 13 or 14, wherein the result of the dysmotility is irritable bowel syndrome and the compound administered is nalmefene.

20. A method for the relief of gastrointestinal dysmotility in a patient afflicted with an idiopathic gastrointestinal dysmotility which comprises administration of an amount which is effective to relieve said dysmotility of a compound represented by the formula:

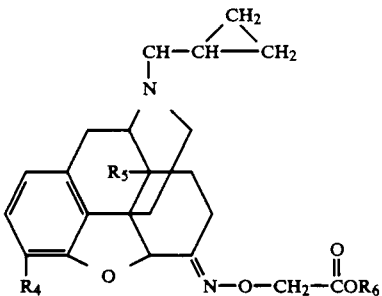

and the corresponding dehydro compounds wherein R₄ is methoxy or hydroxy, R₅ is hydrogen or hydroxy, and R₆ is hydrogen, methyl, ethyl, propyl, allyl and benzyl, and the pharmaceutically acceptable salts thereof.

21. A method as in claim 20 wherein the method of administration is oral and the amount administered is from about 10 to about 50 mg per day.

22. A method as in claim 20 wherein the method of administration is parenteral and the amount administered is from about 10 to about 70 mg per day.

23. A method as in claims 20, 21 or 22 wherein the result of the dysmotility is constipation.

24. A method as in claims 20, 21 or 22 wherein the result of the dysmotility is irritable bowel syndrome.

* * * * *